United States Patent [19]

Kahovec et al.

[11] Patent Number: 4,835,269

[45] Date of Patent: May 30, 1989

[54] SILANE REAGENTS CONTAINING A COMPLEXON GROUP

[75] Inventors: Jaroslav Kahovec; Bedrich Porsch, both of Prague, Czechoslovakia

[73] Assignee: Ceskoslovenska akademie ved, Prague, Czechoslovakia

[21] Appl. No.: 929,590

[22] Filed: Nov. 10, 1986

[30] Foreign Application Priority Data

Nov. 11, 1985 [CS] Czechoslovakia .................. 8111-85
Jan. 10, 1986 [CS] Czechoslovakia .................. 248-86

[51] Int. Cl.[4] .................. C07F 7/18; C07D 265/32
[52] U.S. Cl. .................. 544/69; 556/419
[58] Field of Search .................. 544/69; 556/419

[56] References Cited

U.S. PATENT DOCUMENTS 4,652,598 3/1987 Edelman .................. 556/419

Primary Examiner—John M. Ford
Attorney, Agent, or Firm—Klein & Vibber

[57] ABSTRACT

This invention relates to mixed silane reagents containing a complexon group in the reagent molecule, a method of making said reagents, and porous or nonporous inorganic materials having surface-bound complexon groups which are advantageously modified with the new reagents.

The new mixed silane reagents are of the formula

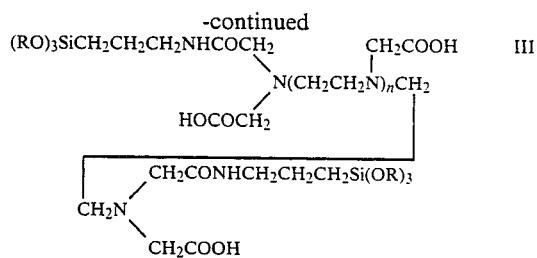

AND

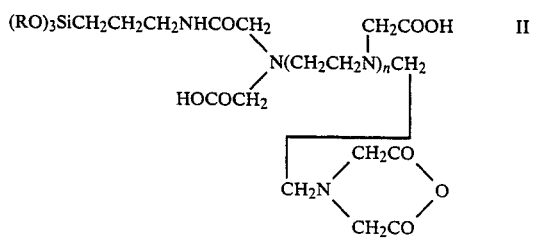

where R is methyl or ethyl and N is 0 or 1. The new reagents are produced by treatment of compounds of the formula $$(RO)_3SiCH_2CH_2CH_2NHR^2$$

where R is methyl or ethyl with a dianhydride of the formula

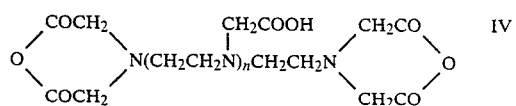

where n is 0 or 1.

The new silane reagents II and III are used for the modification of inorganic materials, such as silicon dioxide, aluminum oxide, titanium dioxide, and glass, to obtain modified materials containing the complexon groups of the formulas

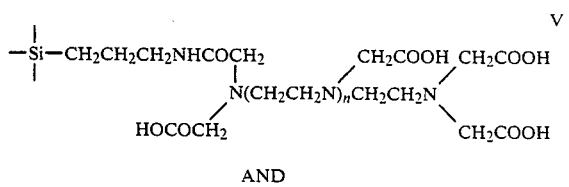

AND

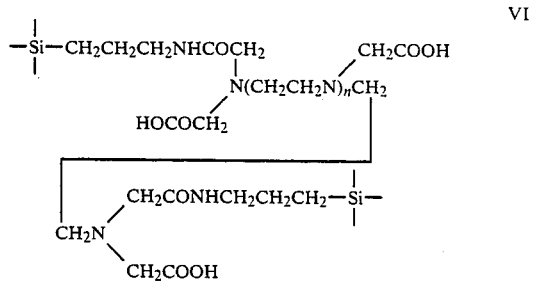

where n is 0 or 1, and where the groups of Formulas V and VI are bound to the surface of the inorganic materials via the silicon atoms, shown above as incomplete valences.

The invention is useful in liquid chromatography, immobilization techniques, and the production of coupling agents for composite materials.

1 Claim, No Drawings

SILANE REAGENTS CONTAINING A COMPLEXON GROUP

This invention relates to silane reagents containing a complexon group in the reagent molecule, a method of making said reagents, and porous or nonporous inorganic materials modified with the new reagents to advantageously incorporate surface-bound complexon groups.

BACKGROUND OF THE INVENTION

Silane reagents are used in the preparation of composite materials and for introducing or immobilizing suitable functional groups on silica and other inorganic materials. These inorganic materials, such as silica gel, porous glass, alumina, or titanium dioxide, when modified with organosilicon compounds that introduce various organic functional groups onto their surface, are useful in many technical fields, such as liquid chromatography, immobilization of enzymes, heterogeneous catalysis, and the preparation of filled polymers or laminates. See, K. K. Unger, *Porous Silica*, Elsevier (New York: 1979).

Silane reagents with chelating functional groups, such as reagents of 8-hydroxyquinoline and ethylenediamine, are known and described in the literature, e.g., E. P. Plueddemann, *Silane Coupling Agents*, Plenum Press (New York: 1980). Some of these reagents are used commercially.

Efficient and commercially successful silane reagents containing a complexon group based on ethylenediaminetetraacetic acid (EDTA) or diethylene triamine pentaacetic acid (DTPA) have been heretofore unknown. The closest known reagents are those containing iminodiacetic acid as the functional chelating group. See *Chromatographia*, Vol. 17, 200 (1983).

Iminodiacetic silane reagents of the formula

are known, where $R^1$ is methyl or ethyl, R is H or $CH_2COOH$, M is H or alkaline metal, n is 0 or 1, and m is 1 or 2. See, U.S. Pat. No. 4,071,546. These reagents are prepared by carboxymethylation of the corresponding amine with sodium chloroacetate in aqueous medium.

The main disadvantage of these known reagents is their low chelating ability, caused by the low number of donor sites in the iminodiacetic acid derivatives and by incomplete carboxymethylation in the ethylenediamine derivatives.

There are also serious disadvantages associated with the preparation of the known reagents. The synthesis of iminodiacetic acid reagents comprises several relatively complex steps. The ethylenediamine derivatives are not chemically homogeneous. In both cases, carboxymethylation of the amino groups is carried out in an aqueous medium, which results in the uncontrolled hydrolysis of alkoxy groups with the formation of silanols, which then spontaneously condense into siloxane oligomers.

Attempts to produce silane reagents and modified inorganic materials incorporating the more powerful chelating derivatives of EDTA and DTPA have not been very successful. A suitable complexon compound modified with alkoxysilyl or chlorosilyl, thereby enabling simple and efficient production and processing, has eluded discovery. Preparation of suitable EDTA or DTPA derivatives of inorganic materials via 3-aminopropyl or 3-glycidyloxypropyl derivatives has also been unsuccessful, primarily because the polymeranalogous reaction is very slow, does not proceed quantitatively, the resulting material surface is considerably heterogeneous with respect to functional interactions, and only a low chelation capacity is achieved.

Known polymeric complexons containing EDTA or DTPA, as described for example in U.S. Pat. No. 4,343,920, are also unsuitable. These materials swell, and have a low mechanical stability. In addition, the functional chelating group frequently appears within the material and not only on the surface. As a result, equilibrium in the chelation of cations is achieved slowly.

SUMMARY OF THE INVENTION

The new mixed silane reagents are mixtures of the substances of the formula

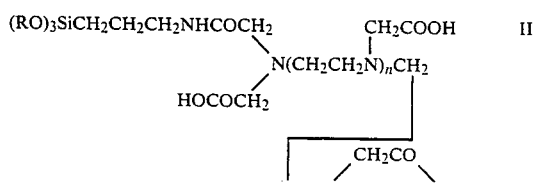

AND

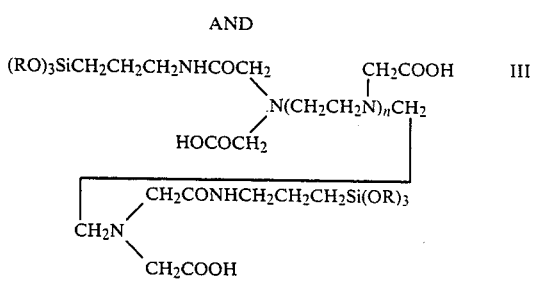

where R is methyl or ethyl and n is 0 or 1. The new reagents are produced by treatment of a compound of the formula

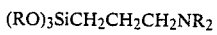

where R is methyl or ethyl with a dianhydride of the formula

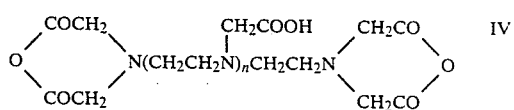

where n is 0 or 1.

The new mixed silane reagents II and III are used for the modification of inorganic materials, such as silicon dioxide, aluminum oxide, titanium dioxide, and glass, to obtain modified materials containing the complexon groups of the formulas

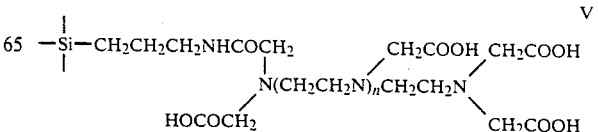

-continued

AND

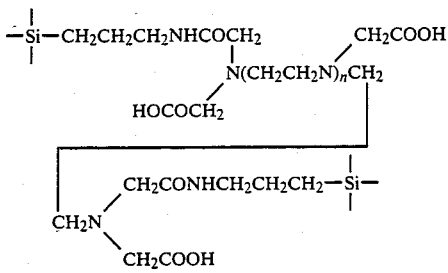

VI where n is 0 or 1, and where the groups of Formulas V and VI are bound to the surface of the inorganic materials via the silicon atoms, shown above as incomplete valences.

The invention is useful in liquid chromatography, immobilization techniques, and in the production of coupling agents for composite materials.

DETAILED DESCRIPTION OF THE INVENTION

It is an object of the invention to overcome the disadvantages of known chelating agents, and to provide advantageous silane reagents containing the chemically bound polydonor complexon of the formulas II and III, prepared by reacting a silane compound of Formula I with a complexon dianhydride of Formula IV, as set forth above.

The new mixed silane complexon reagents exhibit significant advantages in comparison with known reagents. Their chelating ability with respect to metal ions is considerably high, and the stability of the metal chelates formed approaches the stability of EDTA chelates. The new reagents are uniform and homogeneous with respect to functionality: they do not contain any chelating agent other than those of Formulas II and III. The new reagents are synthesized in an anhydrous medium, which advantageously avoids the production of undesirable silanol byproducts (via hydrolysis of the compounds of Formulas II and III) and condensation byproducts from such silanols. The reagents prepared according to the invention retain non-hydrolyzed alkoxy groups, which permits their controlled hydrolysis during reaction of the new reagents with inorganic substrates, such as silica. In this manner, the surface concentration of complexon groups in the final product can be easily controlled. Moreover, the entire procedure is simple, and requires only readily available and inexpensive raw materials.

The invention may be used to introduce complexon groups into silica and other organic materials, such as silica gel, kieselgur, glass, alumina, or titanium dioxide. The reagents can also be used as coupling agents, to improve the adhesion of composite materials comprising metal and glass, metal and titanium dioxide, etc.

The invention also provides for the surface modification of inorganic materials via chemically bound complexon groups. A porous or nonporous inorganic material selected from among silicon dioxide, aluminum oxide, titanium dioxide, and glass is modified, by treatment with the new reagent of Formulas I and II, to introduce chemically bound complexon groups of the Formulas V and VI to the surface of the inorganic material. The modified materials are easily prepared in a single step such that only the functional groups of Formulas V and VI are bound to the surface, by a strong chemical bond.

The necessary inorganic substrates are commonly available, and their choice depends on the desired applications. For example, silica gels with an average particle size of 3 to 50 $\mu$m and a specific surface area of 5 to 600 m$^2$/g are suitable for liquid chromatography.

The reaction of the substrate with the organosilicon reagent proceeds between hydroxyl groups of the substrate and the alkoxyl or hydroxyl group (formed by hydrolysis) of the new reagents II and III.

For example, when n=0:

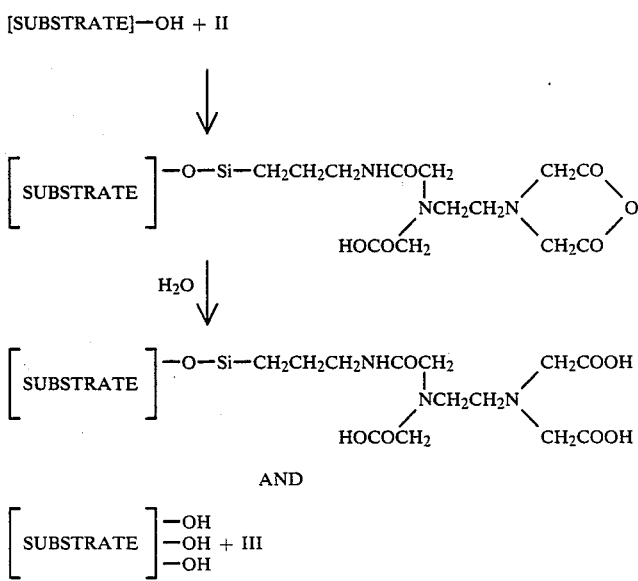

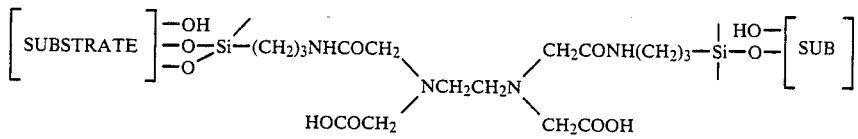

In this manner, a strong chemical bond to the surface of the substrate is formed, and the resulting surface product contains the complexon groups V and VI.

The reaction may be performed in polar solvents, such as alcohols, dimethylformamide, pyridine and water, at a temperature at 15° C. up to the boiling point of the solvent. After reaction, the modified materials are preferably washed with solvents to remove the excess reagent, and they are dried.

The invention is further described with reference to the following examples. It will be understood by skilled practitioners that these examples are illustrative, and do not serve to limit the scope of the invention or the appended claims.

EXAMPLE 1

5.1 g of dianhydride of EDTA are suspended in 30 ml of anhydrous pyridine, and 2.3 g of 3-aminopropyltriethoxysilane is added dropwise under stirring. The reaction mixture is stirred at ambient temperature for 12 hours. The unreacted dianhydride is then removed by filtration and is washed with anhydrous pyridine. Pyridine is removed from the combined filtrates by distillation in vacuum. The residue contains a mixture of the compounds of formulas II and III in a ratio of about 1:1, as verified by mass balance (stoichiometry) and NMR spectra.

EXAMPLE 2

13 g of silica gel with a particle size of 10 um and a specific surface area of 450 m²/g are introduced to a 300 ml methanol solution containing 15 g of mixed silanes of Formulas II and III (R=ethyl, n=0). The mixture is allowed to react at laboratory temperature for 240 hours, with occasional stirring. The resulting product is filtered, washed with methanol, water and methanol, and is dried for 3 hours at 85° C. The exchange capacity is 0.63 mmol $Cu^{++}$/g.

EXAMPLE 3

A 13 g mixture of silanes according to Example 2 is dissolved in 300 ml of distilled water at 45° C. 13 g of silica gel is added, as in Example 2. The mixture is heated for 8 hours at 80° C. The product is filtered, washed with water and methanol, and is dried for 3 hours at 85° C. The exchange capacity is 0.51 mmol $Cu^{++}$/g.

EXAMPLE 4

The procedure is performed as in Example 2, except that porous glass is used instead of silica gel.

EXAMPLE 5

The procedure is performed as in Example 3, except that aluminum oxide is used instead of silica gel.

EXAMPLE 6

The procedure is performed as in Example 2, except that titanium dioxide is used instead of silica gel.

We claim:

1. A silane reagent comprising a chemically bound polydonor complexon selected from the group consisting of

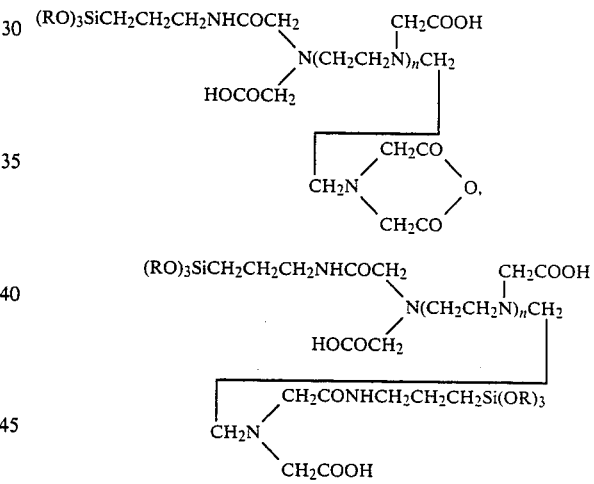

and a combination thereof, where R is selected from the group consisting of methyl and ethyl and n is an integer of 0 or 1.

* * * * *